(12) United States Patent
Hosaka et al.

(10) Patent No.: US 7,169,878 B2
(45) Date of Patent: Jan. 30, 2007

(54) DIAMINES, POLYIMIDE PRECURSORS AND POLYIMIDES PRODUCED BY USING THE DIAMINES, AND LIQUID CRYSTAL ALIGNING AGENTS

(75) Inventors: Kazuyoshi Hosaka, Chiba (JP); Hideyuki Nawata, Chiba (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 80 days.

(21) Appl. No.: 10/450,841

(22) PCT Filed: Dec. 26, 2001

(86) PCT No.: PCT/JP01/11488

§ 371 (c)(1),
(2), (4) Date: Jun. 26, 2003

(87) PCT Pub. No.: WO02/051909

PCT Pub. Date: Jul. 4, 2002

(65) Prior Publication Data

US 2004/0054096 A1    Mar. 18, 2004

(30) Foreign Application Priority Data

Dec. 26, 2000  (JP)  ............... 2000-394139

(51) Int. Cl.
*C08G 73/10* (2006.01)
*C08G 69/26* (2006.01)

(52) U.S. Cl. ............ 528/170; 528/353; 528/125; 528/128; 528/172; 528/173; 528/174; 528/176; 528/179; 528/183; 528/185; 528/188; 528/220; 528/229; 528/350; 525/420; 525/432; 525/436; 428/1.1; 428/1.2; 428/1.26; 428/473.5

(58) Field of Classification Search ............ 528/170, 528/353, 432, 436, 125, 126, 128, 172, 173–174, 528/176, 179, 183, 185, 188, 350, 351; 428/1.2, 428/1.26, 473.5, 1.1; 525/432, 436
See application file for complete search history.

(56) References Cited

U.S. PATENT DOCUMENTS

| | | | |
|---|---|---|---|
| 5,608,033 A | 3/1997 | Nihira et al. | |
| 5,665,856 A | 9/1997 | Nihira et al. | |
| 5,861,534 A | 1/1999 | Nihira et al. | |
| 6,111,059 A * | 8/2000 | Nihira et al. | 528/353 |
| 6,500,913 B2 * | 12/2002 | Mathew et al. | 528/170 |
| 6,740,371 B1 * | 5/2004 | Hosaka et al. | 428/1.2 |
| 2004/0048004 A1 * | 3/2004 | Hosaka et al. | 428/1.26 |

FOREIGN PATENT DOCUMENTS

| | | |
|---|---|---|
| EP | 0 679 633 | 11/1995 |
| EP | 682283 | 11/1995 |
| EP | 0 905 167 | 3/1999 |
| JP | 3-121132 | 5/1991 |
| JP | 2000-302868 | 10/2000 |

OTHER PUBLICATIONS

Patent Abstracts of Japan, JP 2000-302868, Oct. 31, 2000.

* cited by examiner

*Primary Examiner*—P. Hampton Hightower
(74) *Attorney, Agent, or Firm*—Oblon, Spivak, McClelland, Maier & Neustadt, P.C.

(57) ABSTRACT

A diamine compound represented by the formula (1):

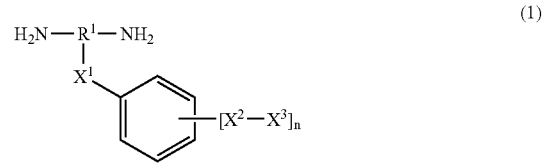

wherein $R^1$ is a trivalent organic group, each of $X^1$ and $X^2$ is a bivalent organic group, $X^3$ is an alkyl or fluoroalkyl group having from 1 to 22 carbon atoms, or a cyclic substituent selected from aromatic rings, aliphatic rings, heterocyclic rings and their substituted groups, and n is an integer of from 2 to 5. And, a polyimide precursor and a polyimide synthesized by using the diamine compound; and a treating agent for liquid crystal alignment containing the polyimide precursor and/or the polyimide.

12 Claims, No Drawings

DIAMINES, POLYIMIDE PRECURSORS AND POLYIMIDES PRODUCED BY USING THE DIAMINES, AND LIQUID CRYSTAL ALIGNING AGENTS

TECHNICAL FIELD

The present invention relates to a novel diamine compound, a polyimide precursor and a polyimide synthesized by using the compound as a part of the materials and a treating agent for liquid crystal alignment containing such a polymer.

BACKGROUND ART

A polyimide has been widely used as a protective material or an insulating material in the electric or electronic field by virtue of its characteristics such as high mechanical strength, heat resistance and solvent resistance. Especially in an application to an alignment film to be used for a liquid crystal display device, it has been common to employ a polyimide because of the simplicity in film formation and the uniformity and durability of the coating film surface.

However, in recent years, developments in the electric and electronic fields have been remarkable, and higher properties have been correspondingly required for the material to be employed. Under these circumstances, also for a liquid crystal alignment film, it has been required to impart new properties which conventional polyimides do not have, in attempts for high densification and high performance of the displays.

One of the properties required for a liquid crystal alignment film is an ability to provide a high pretilt angle. As a means to obtain a high pretilt angle required for a polyimide liquid crystal alignment film, JP-A-64-25126 and JP-A-5-27244 propose a treating agent for liquid crystal alignment comprising a polyimide precursor or a polyimide having a side chain, prepared by using, as a material, a diamine having a long chain alkyl group, etc. However, the diamine proposed in these references, has had a problem with respect to the low level in efficiency to increase the pretilt angle relative to the amount introduced, or in the reactivity.

When properties other than the pretilt angle, are also to be imparted to the liquid crystal alignment film, the amount of the diamine introduced to increase the pretilt angle should better be small, as the degree of freedom in polymer design will thereby be broadened. However, if the amount the diamine introduced, is too small, it becomes impossible to secure the required pretilt angle.

Further, in a case where a very high pretilt angle of from 20° to 90° is required, it is necessary to introduce a large amount of a diamine to increase the pretilt angle. Accordingly, if the reactivity of the diamine is low, it takes time for the polymerization of the polymer, or in some cases, polymerization may not substantially proceed. Taking time for the polymerization is industrially problematic, and if the polymerization degree of the polymer is inadequate, such will be a problem from the viewpoint of the durability as a liquid crystal alignment film.

In view of the above problems, the present invention is to provide a novel diamine compound which is highly effective to increase the pretilt angle even in a small amount and excellent in the polymerization reactivity, a polyimide precursor or a polyimide synthesized by using such a diamine compound as a part of the material, and a treating agent for liquid crystal alignment containing such a polymer.

DISCLOSURE OF THE INVENTION

As a result of an extensive study on the above-mentioned problems, the present inventors have found a diamine compound having a specific structure, a polyimide precursor or a polyimide synthesized by using such a diamine compound as a part of the material, and a treating agent for liquid crystal alignment containing such a polymer.

Namely, the present invention relates to a diamine compound represented by the formula (1):

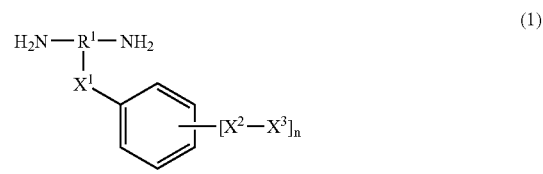

wherein $R^1$ is a trivalent organic group, each of $X^1$ and $X^2$ is a bivalent organic group, $X^3$ is an alkyl or fluoroalkyl group having from 1 to 22 carbon atoms, or a cyclic substituent selected from aromatic rings, aliphatic rings, heterocyclic rings and their substituted groups, and n is an integer of from 2 to 5; a polyimide precursor and a polyimide synthesized by using such a diamine compound as a part of the material; and a treating agent for liquid crystal alignment containing such a polymer.

BEST MODE FOR CARRYING OUT THE INVENTION

Now, the present invention will be described in detail.

In the formula (1), $R^1$ is not particularly limited so long as it is a trivalent organic group. However, from the viewpoint of the nucleophilic reactivity of amino groups, it is preferred that the amino groups are bonded to an aromatic ring, and for example, a structure represented by the following formula (2) may be mentioned:

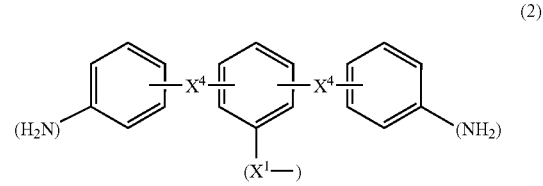

wherein $X^4$ is selected from a single bond, an ether bond (—O—), an ester bond (—COO—), a reversed ester bond (—OCO—), an amido bond (—CONH—) and a reversed amido bond (—NHCO—), and the bonding position of $X^4$ may be any position of opposition, p-position or m-position to the amino group and to $X^1$.

Further, with a view to not lowering the density of side chain substituents when formed into a polymer, $R^1$ is particularly preferably a phenyl ring.

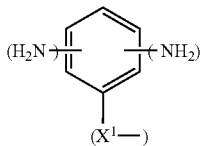

In the formula (1), $X^1$ is not particularly limited so long as it is a bivalent organic group, and it is preferably an organic group selected from a single bond, —O—, —OCH$_2$—, —CH$_2$O—, —COOCH$_2$— and —CH$_2$OOC—, more preferably —O—, —OCH$_2$—, —COOCH$_2$— or —CH$_2$OOC—, which is easy to synthesize.

In the formula (1), $X^2$ is not particularly limited, so long as it is a bivalent organic group, and it is preferably a single bond or —O—, particularly preferably —O—.

In the formula (1), $X^3$ is an alkyl or fluoroalkyl group having from 1 to 22 carbon atoms, or a cyclic substituent selected from aromatic rings, aliphatic rings, heterocyclic rings and their substituted groups, but it is preferably an alkyl group having from 6 to 22 carbon atoms or a fluoroalkyl group having from 1 to 22 carbon atoms.

In the formula (1), the number n of side chain substituents introduced, is an integer of from 2 to 5, but preferably, the introduced number n is 2.

As described in the foregoing, the diamine compound of the present invention is characterized in that at least two side chain substituents are introduced into the diamine structure so that the effect of the side chains would be substantial even when a small introduced amount, and the sites of the side chain substituents are distanced from the amino groups as shown in the formula (1) in order not to impair the polymerization reactivity.

The diamine compound of the present invention is easy to synthesize and is useful as a material for a polyimide precursor and a polyimide, etc. Further, a polyimide precursor or polyimide synthesized by using it as a part of the material, is excellent in the effect to increase the pretilt angle, and thus, is useful for a treating agent for liquid crystal alignment.

Synthesis of the Diamine Compound

The diamine compound represented by the formula (1) of the present invention can be obtained by synthesizing the corresponding dinitro compound of the formula (3) and further reducing the nitro groups to convert them to amino groups.

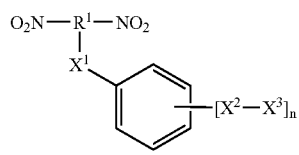

wherein $X^1$, $X^2$, $X^3$ and n are the same as those shown in the formula (1).

The method for reducing the dinitro compound is not particularly limited, and it is usually carried out by e.g. hydrogen gas, hydrazine or hydrogen chloride in a solvent such as ethyl acetate, toluene, tetrahydrofuran, dioxane or an alcohol by using, as a catalyst, palladium-carbon, platinum oxide Raney Nickel, platinum black, rhodium-alumina, platinum sulfide-carbon or the like.

The dinitro compound of the formula (3) can be obtained by a method of bonding at least two substituents $X^3$ via connecting portions $X^2$ to a phenyl ring and then bonding the dinitro portion thereto via a connecting portion $X^1$.

The connecting portion $X^1$ is a bonding group such as a single bond, an ether bond (—O—), an ether methylene bond (—OCH$_2$—), a methylene ether bond (—CH$_2$O—), an ester bond (—COO—), a reversed ester bond (—OCO—), an ester methylene bond (—COOCH$_2$—), a methylene ester bond (—CH$_2$COO—), an amido bond (—CONH—) or a reversed amido bond (—NHCO—). Such a bonding group may be formed by a usual organic synthetic method. Specifically, in the case of the ether or ether methylene bond, it is common to employ a method wherein the corresponding dinitro group-containing halogen derivative is reacted with a hydroxyl group-substituted benzene derivative containing the connecting portions $X^2$ and the substituents $X^3$, in the presence of an alkali, or a method wherein the dinitro group-containing hydroxyl group derivative is reacted with a halogen-substituted benzene derivative containing the connecting portions $X^2$ and the substituents $X^3$, in the presence of an alkali.

In the case of the ester or ester methylene bond, it is common to employ a method wherein the corresponding dinitro group-containing acid chloride is reacted with a hydroxyl group-substituted benzene derivative containing the connecting portions $X^2$ and the substituents $X^3$, in the presence of an alkali.

In the case of the amido bond, it is common to employ a method wherein the corresponding dinitro group-containing acid chloride compound is reacted with an amino group-substituted benzene derivative containing the connecting portions $X^2$ and the substituents $X^3$, in the presence of an alkali.

In the case of the single bond, various methods are available, but bonding may be optionally carried out by a common organic synthetic method such as a Grignard reaction, a Friedel-Crafts acylation method of an aromatic ring or a Kishner reduction method.

The connecting portion $X^1$ can be selected from the above-mentioned bonding groups, but it is preferably an ether bond (—O—), an ether methylene bond (—OCH$_2$—), an ester bond (—COO—), an ester methylene bond (—COOCH$_2$—) or an amido bond (—CONH—), which can easily be synthesized.

As the dinitro group-containing halogen derivative and the dinitro group-containing derivative, constituting the trivalent organic group $R^1$, a 1-halogen group-substituted dinitroalkylene compound, a 1-hydroxyl group-substituted dinitroalkylene compound, 2,4-dinitro-1-naphthol, 3,5-dinitrochlorobenzene, 2,4-dinitrochlorobenzene, 2,4-dinitrofluorobenzene, 3,5-dinitrobenzoic acid chloride, 3,5-dinitrobenzoic acid, 2,4-dinitrobenzoic acid chloride, 2,4-dinitrobenzoic acid, 3,5-dinitrobenzyl chloride, 2,4-dinitrobenzyl chloride, 3,5-dinitrobenzyl alcohol, 2,4-dinitrobenzyl alcohol, 2,4-dinitroaniline, 3,5-dinitroaniline, 2,6-dinitroaniline, 2,4-dinitrophenol, 2,5-dinitrophenol, 2,6-dinitrophenol and 2,4-dinitrophenol acetic acid, may, for example, be mentioned. A combination of these compounds may suitably be selected depending upon the particular purpose in view of the reaction or the availability of the material. It should be mentioned that the compounds mentioned here are merely exemplary.

The hydroxyl group-substituted benzene derivative containing the connecting portions $X^2$ and the substituents $X^3$ can be obtained by a usual organic synthetic method. Specifically, it is common to employ a method of reducing a methyl benzoate group by means of $LiAlH_4$, or reacting a benzaldehyde group with formaldehyde in the presence of an alkali.

The connecting portion $X^2$ is a single bond or an ether bond (—O—), preferably an ether bond (—O—) which can easily be synthesized. Such a bonding group can be formed by a usual organic synthetic method. Specifically, it is common to employ a method of reacting a hydroxyl group-substituted benzene derivative with a halogen derivative containing the corresponding substituent $X^3$ in the presence of an alkali, or a method of reacting a halogen-containing benzene derivative with an alcohol derivative containing the corresponding substituent $X^3$ in the presence of an alkali. Further, in the case of a single bond, various method are available, but bonding can suitably be carried out by means of a common organic synthetic method such as a Grignard reaction, a Friedel-Crafts acylation method of an aromatic ring or a Kishner reduction method.

The substituent $X^3$ is an alkyl or fluoroalkyl group having from 1 to 22 carbon atoms, preferably an alkyl group having at least 6 carbon atoms or a fluoroalkyl group having at least one carbon atom, substantially an alkyl group having from 6 to 22 carbon atoms or a fluoroalkyl group having from 1 or 22 carbon atoms, from the viewpoint of efficiency in the synthesis. The larger the carbon number, the higher the effect to increase the water repellency of the polyimide precursor and the polyimide, and further, when it is used for an application to a liquid crystal alignment film, the effect to increase the pretilt angle will be higher.

Further, depending upon the purpose, the substituent $X^3$ may be a cyclic substituent selected from aromatic rings, aliphatic rings, heterocyclic rings and their substituted groups. Specific examples include a benzene ring, a heterocyclic ring, a cyclohexane ring, a biphenyl ring, a terphenyl ring, a bicyclohexyl ring, a tercyclohexyl ring, a phenylcyclohexyl ring, a phenylpyridine ring, a cyclohexylpyridine ring, a phenyldioxane ring, a phenylpyrimidine ring, a cyclohexylpyrimidine ring, a phenylpyrazine ring, a cyclohexylpyrazine ring, and further one having these cyclic compounds bonded via a connecting portion such as ethylene, acetylene, an ester, oxymethylene, azo, azoxy or azomethine. It is particularly preferred to employ a benzene ring, a cyclohexane ring, a biphenyl ring, a bicyclohexyl ring or a phenylcyclohexyl ring from the viewpoint of availability of the material or efficiency in the synthetic reaction.

Further, it is common that these cyclic compounds are substituted by various terminal groups. As such terminal groups, an alkyl group, an alkoxy group, a fluoroalkyl group, a fluoroalkoxy group, a halogen atom, a nitro group, an amino group, a cyano group, an azo group, a formyl group, an acetyl group and an acetoxy group are, for example, known. From the viewpoint of availability of the material, efficiency in the synthetic reaction and an ability to effectively provide a pretilt angle, particularly preferred is a substituted cyclic group which is substituted by a substituent selected from an alkyl group, an alkoxy group, a fluoroalkyl group and a fluoroalkoxy group. Such a substituted cyclic group may be suitably selected to increase the heat resistance, water repellency, etc. of the polyimide precursor and the polyimide.

In the formula (1), n is an integer of from 2 to 5, and the number n of side chain substituents to be introduced, may be suitably selected to improve the properties such as heat resistance, water repellency, etc. of the polyimide precursor and the polyimide. Preferred is introduction of side chain substituents so that $X^2$ which is easy to synthesize, is bonded to each of the two m-positions to $X^1$.

As one of preferred examples of the diamine compound represented by the formula (1), the following formula (4) is shown, and as one of more preferred examples, the formula (5) is shown.

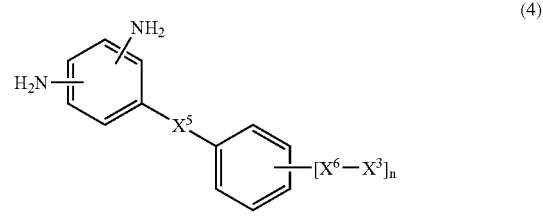

(4)

wherein $X^5$ is a bivalent organic group selected from a single bond, —O—, —OCH$_2$—, —CH$_2$O—, —COOCH$_2$— and —CH$_2$OOC—, $X^6$ is a bivalent organic group selected from a single bond and —O—, and $X^3$ is an alkyl or fluoroalkyl group having from 1 to 22 carbon atoms, or a cyclic substituent selected from aromatic rings, aliphatic rings, heterocyclic rings and their substituted groups, and n is an integer of from 2 to 5.

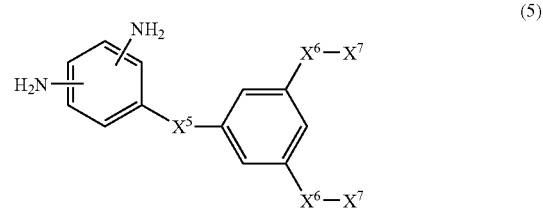

(5)

wherein $X^5$ is a bivalent organic group selected from a single bond, —O—, —OCH$_2$—, —CH$_2$O—, —COOCH$_2$— and —CH$_2$OOC—, $X^6$ is a bivalent organic group selected from a single bond and —O—, and $X^7$ is an alkyl group having from 6 to 22 carbon atoms, or a fluoroalkyl group having from 1 to 22 carbon atoms.

The diamine compound of the present invention represented by the formula (1) obtained by the method as described above, may be subjected to polycondensation with a tetracarboxylic acid or its derivative such as tetracarboxylic acid, tetracarboxylic dihalide or tetracarboxylic dianhydride, to obtain a polyimide precursor or a polyimide having a specific structure in the side chains.

Polyimide Precursor and Polyimide

As mentioned above, the polyimide precursor and the polyimide of the present invention can be obtained by a polycondensation reaction of a diamine compound represented by the formula (1) with a tetracarboxylic acid or its derivative.

The tetracarboxylic acid or its derivative to be used at that time is not particularly limited. Their specific examples include aromatic tetracarboxylic acids such as pyromellitic acid, 2,3,6,7-naphthalene tetracarboxylic acid, 1,2,5,6-naphthalene tetracarboxylic acid, 1,4,5,8-naphthalene tetracarboxylic acid, 2,3,6,7-anthracene tetracarboxylic acid, 1,2,5,6-anthracene tetracarboxylic acid, 3,3',4,4'-biphenyl tetracarboxylic acid, 2,3,3',4-biphenyl tetracarboxylic acid, bis(3,4-dicarboxyphenyl)ether, 3,3',4,4'-benzophenone tetracarboxylic acid, bis(3,4-dicarboxyphenyl)sulfone, bis(3,4-dicarboxyphenyl)methane, 2,2-bis(3,4-dicarboxyphenyl) propane, 1,1,1,3,3,3-hexafluoro-2,2-bis(3,4-dicarboxyphenyl)propane, bis(3,4-dicarboxyphenyl) dimethylsilane, bis(3,4-dicarboxyphenyl)diphenylsilane, 2,3,4,5-pyridine tetracarboxylic acid and 2,6-bis(3,4-dicarboxyphenyl)pyridine, and their dianhydrides and their dicarboxylic diacid halides; alicyclic tetracarboxylic acids such as 1,2,3,4-cyclobutane tetracarboxylic acid, 1,2,3,4-cyclopentane tetracarboxylic acid, 1,2,4,5-cyclohexane tetracarboxylic acid, 2,3,5-tricarboxy cyclopentylacetic acid, 3,4-dicarboxy-1,2,3,4-tetrahydro-1-naphthalene succinic acid, bicyclo[3,3,0]-octane-tetra-carboxylic acid and 3,5,6-tricarboxynorbornane, and their dianhydrides and their dicarboxylic diacid halides; and aliphatic tetracarboxylic acids such as 1,2,3,4-butane tetracarboxylic acid, and their dianhydrides and their dicarboxylic diacid halides.

These tetracarboxylic acids and their derivatives may be used alone or in combination as a mixture of two or more of them.

Further, a polyimide obtainable by using an alicyclic tetracarboxylic acid or an aliphatic tetracarboxylic acid, or a dianhydride or dicarboxylic diacid halide thereof as a part or whole of the entire tetracarboxylic acid or its derivative, can be made to be a solvent-soluble polyimide. Particularly, polyimides obtainable by using 2,3,5-tricarboxy cyclopentyl acetic acid, 3,4-dicarboxy-1,2,3,4-tetrahydro-1-naphthalene succinic acid, bicyclo[3,3,0]-octane-tetracarboxylic acid, 1,2,3,4-butane tetracarboxylic acid, and their dianhydrides and their dicarboxylic diacid halides, show good solubility in organic polar solvents such as N-methyl pyrrolidone, N,N'-dimethyylacetoamide, N,N'-dimethylformamide and γ-butyrolactone.

In an application to liquid crystal alignment film, alicyclic tetracarboxylic acids and their dianhydrides and their dicarboxylic diacid halides are preferred from the viewpoint of the transparency of the coating film. Particularly preferred are 1,2,3,4-cyclobutane tetracarboxylic dianhydride, 3,4-dicarboxy-1,2,3,4-tetrahydro-1-naphthalene succinic dianhydride, bicyclo[3,3,0]-octane-tetracarboxylic dianhydride, 3,5,6-tricarboxynorbornane-2:3,5:6 dianhydride, and 2,3,5-tricarboxy cyclopentyl acetic dianhydride.

For the polyimide precursor and the polyimide of the present invention, the diamine component may be a copolymer of the diamine compound represented by the formula (1) (hereinafter referred to simply as the diamine (1)) with a common diamine other than that (hereinafter referred to simply as a common diamine).

The common diamine to be used in such a case, is usually a primary diamine to be used for the synthesis of a polyimide and is not particularly limited. Its specific examples include aromatic diamines such as p-phenylenediamine, m-phenylenediamine, 2,5-diaminotoluene, 2,6-diaminotoluene, 4,4'-diaminobiphenyl, 3,3'-dimethyl-4,4'-diaminobiphenyl, 3,3'-dimethoxy-4,4'-diaminobiphenyl, diaminodiphenyl methane, diaminodiphenyl ether, 2,2-diaminodiphenyl propane, bis(3,5-diethyl-4-aminophenyl) methane, diaminodiphenyl sulfone, diaminobenzophenone, diaminonaphthalene, 1,4-bis(4-aminophenoxy)benzene, 1,4-bis(4-aminophenyl)benzene, 9,10-bis(4-aminophenyl)anthracene, 1,3-bis(4-aminophenoxy)benzene, 4,4'-bis(4-aminophenoxy)diphenylsulfone, 2,2-bis[4-(4-aminophenoxy)phenyl] propane, 2,2-bis[4-(4-aminophenoxy)phenyl]hexafluoropropane, alicyclic diamines such as bis(4-aminocyclohexyl) methane and bis(4-amino-3-methylcyclohexyl)methane, and aliphatic diamines such as tetramethylenediamine and hexamethylenediamine, as well as diaminocyloxane shown by:

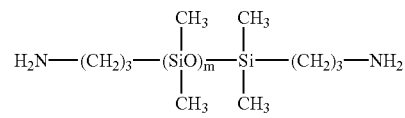

wherein m is an integer of from 1 to 10. Further, these diamines may be used alone or in combination as a mixture of two or more of them.

By adjusting the proportion of the mols of the diamine (1) to the total mols of the diamines to be used, at the time of obtaining the polyimide precursor and the polyimide of the present invention, it is possible to modify the surface properties of these polymers such as water repellency, and further, in a case where they are used as liquid crystal alignment films, it is possible to improve the wettability with liquid crystal and further to increase the pretilt angle of liquid crystal. The proportion of the mols of the diamine (1) to the total mols of diamines to be used in such a case, is at least 1 mol %.

Further, when they are used as liquid crystal alignment films, as the pretilt angle required in a usual liquid crystal display system (for example, a Twisted Nematic system, etc.), from about a few degrees to about ten degrees is used in many cases. Accordingly, the proportion of the mols of the diamine (1) to the total mol of diamines to be used is within a range of from 1 mol % to 49 mol %. Further, in the case of a vertical alignment system, the proportion of the mols of the diamine (1) is usually from 25 mol % to 100 mol %.

Further, the diamine (1) of the present invention is highly effective to improve the tilt angle, and even in a case of a vertical alignment system, it is not necessary to use the diamine (1) in a proportion of 100 mol %, and by copolymerizing a diamine having other properties, it is possible to impart additional properties.

The polycondensation reaction of a tetracarboxylic acid or its derivative with the above diamine to obtain the polyimide precursor and the polyimide of the present invention, is not particularly limited, and a usual synthetic method for a polyimide can be employed.

A method is common in which a tetracarboxylic dianhydride is used as a derivative of a tetracarboxylic acid, and it is reacted with a diamine in an organic polar solvent such as N-methylpyrrolidone or N,N'-dimethylacetoamide to obtain a polyamic acid as a polyimide precursor, followed by dehydration ring closure to obtain a polyimide.

As the solvent for the reaction, in addition to the above, N,N-dimethylformanide or γ-butylolactone may, for example, be used. Further, as the reaction temperature during the synthesis of the polyimide precursor, an optional temperature of from −20° C. to 150° C. may be selected, but preferred is within a range of from −5° C. to 100° C.

The ratio of the mols of the tetracarboxylic dianhydride to the mols of the diamine (the total mols of the diamine (1) and the common diamine) is preferably from 0.8 to 1.2. Like a usual polycondensation reaction, as this molar ratio becomes close to 1.0, the polymerization degree of the polymer to be formed, increases.

If the polymerization degree is too small, the strength of the polyimide film tends to be inadequate, and if the polymerization degree is too large, the operation efficiency at the time of formation of a polyimide film is likely to deteriorate. Accordingly, the polymerization degree of the product in this reaction is preferably adjusted to be from 10,000 to 1,000,000 by the weight average molecular weight as measured by gel permeation chromatography.

To convert the polyimide precursor to a polyimide, the dehydration ring closure may be carried out by heating the reaction solution of the polyimide precursor as it is at a temperature of from 100° C. to 400° C., preferably from 120° C. to 250° C., or by means of a catalyst such as pyridine/acetic anhydride. In such a case, it is of course preferred that the polyimide precursor is recovered and washed and then re-dissolved and converted to a polyimide.

Treating Agent for Liquid Crystal Alignment

When the polyimide is to be used as an insulating film or a protecting film for an electric or electronic device or as an alignment film for a liquid crystal display device, it is necessary to form a polyimide film having a uniform thickness on a substrate.

Usually, to form such a polyimide coating film, a method is employed wherein a polyimide precursor solution is coated on a substrate and heated on a substrate for imidation to form a polyimide coating film, or in a case where the polyimide is soluble in a solvent, a solution of the polyimide having the polyimide precursor preliminarily imidated, is coated on a substrate, followed by drying to form a polyimide coating film.

As the temperature for heating on the substrate for imidation, an optional temperature from 100° C. to 400° C. may be employed, but particularly preferred is within a range of from 150° C. to 350° C. In the case of coating and drying the polyimide solution, it is sufficient if the solvent evaporates and is usually sufficient at a temperature of from 80° C. to 150° C.

Coating on a substrate can be carried out by a printer for e.g. screen printing, offset printing or inkjet printing, as well as by a dip coater, a roll coater or a spinner.

With respect to the polyimide precursor solution and the polyimide solution to be used for coating, the reaction solution may be used as it is or after dilution to a proper concentration, or it may be precipitated in a poor solvent such as water, methanol or ethanol, isolated and washed and then re-dissolved in a solvent for use.

The solvent to be used for dilution or re-dissolution is not particularly limited so long as it is capable of dissolving the polyimide precursor or the polyimide. For example, 2-pyrrolidone, N-methylpyrrolidone, N-ethylpyrrolidone, N,N-dimethylacetoamide, N,N-dimethylformamide or γ-butyrolactone may be mentioned. These solvents may be used alone or in combination as a mixture.

Further, even a solvent which is incapable of providing a uniform solution of the polyimide precursor or the polyimide by itself, may be added to the coating solution within a range where a uniform solution can be obtained. As such an example, ethyl cellosolve, butyl cellosolve, ethyl carbitol, butyl carbitol, ethyl carbitol acetate or ethylene glycol may be mentioned. These solvents may be used alone or in combination as a mixture.

It is also preferred to add to the coating solution e.g. a coupling agent for the purpose of improving the adhesion of the polyimide film to the substrate, or a dielectric or electroconductive substance for the purpose of changing electrical properties such as the dielectric constant and electroconductivity of the polyimide film.

The treating agent for liquid crystal alignment of the present invention may be one containing only the polyimide precursor or the polyimide of the present invention as the resin component, or another resin component may be mixed thereto for use. It may, of course, be a mixture of the polyimide precursor and the polyimide of the present invention. To mix the resin components, it is convenient to prepare a mixed solution at the time of preparing the coating solution.

The treating agent for liquid crystal alignment of the present invention is a coating solution containing the polyimide precursor and/or the polyimide of the present invention, prepared as described above. As a method for its use, a coating film is formed on a substrate by the above-mentioned method and then subjected to treatment for alignment by rubbing or light irradiation, or without treatment for alignment, it may be used as a liquid crystal alignment film.

In the case of a liquid crystal alignment film, the film thickness is usually from 0.01 μm to 1.0 μm. Further, it is common to employ a printing machine for the coating of the treating agent for alignment, since the dimensional precision of the coating film and the uniformity of the surface become particularly important.

Now, the present invention will be described in further detail with reference to Examples, but the present invention is by no means restricted thereto.

EXAMPLE 1

Synthesis of Diamine {5}

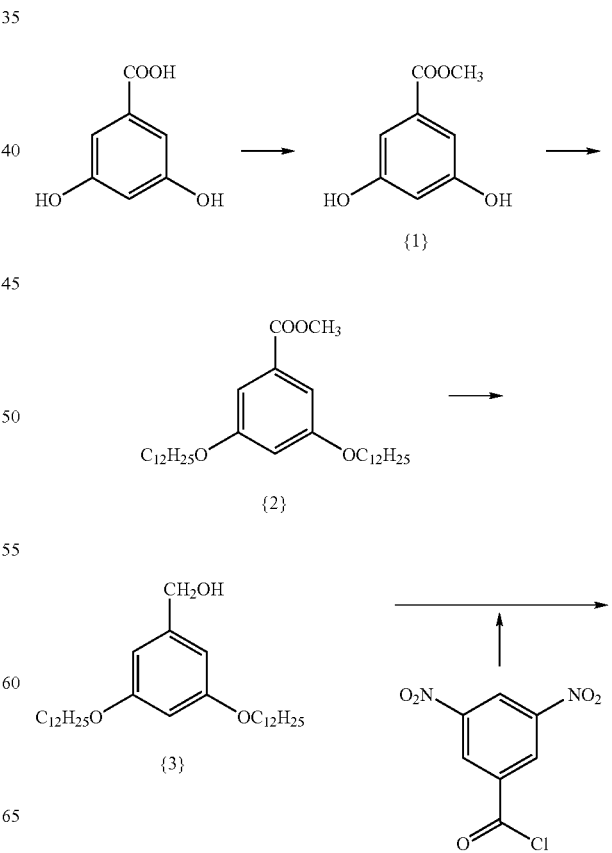

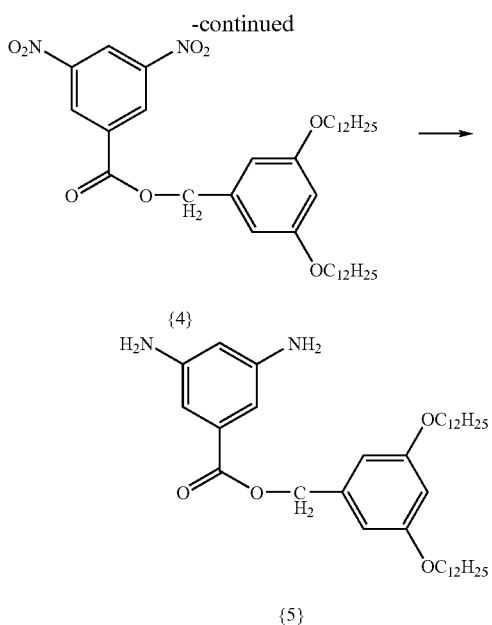

{4}

{5}

Into a 3,000 ml eggplant type flask, 3,5-dihydroxy benzoic acid (120.76 g), concentrated sulfuric acid (6.8 ml) and methanol (1360 ml) were added, and refluxed and stirred for 24 hours. After completion of the reaction, the reaction solution was distilled off under reduced pressure. The residue was washed with water to obtain colorless crystals {1} (71.78 g, 55%, mp: 181–182° C.).

$^1$H-NMR(d-DMSO, δppm): 9.58(2H,S), 6.75(2H,S), 6.37 (1H,S), 3.73(3H,S).

Into a 500 ml three necked flask, {1} (20.03 g), 1-bromododecane (65.21 g), potassium carbonate (36.20 g) and DMF (400 ml) were added, followed by stirring at 100° C. for 24 hours. After completion of the reaction, the reaction solution was filtered while it was hot. The filtrate was left to stand at room temperature, and precipitated solid was collected by filtration to obtain colorless crystals {2} (57.16 g, 95%, mp: 84–86° C.).

$^1$H-NMR(CDCl$_3$, δppm): 7.16(2H,S), 6.63(1H,S), 3.96 (4H,t), 3.98(3H,S), 1.77(4H,m), 1.45(4H,m), 1.27(32H, broad), 0.88(6H,t).

In a nitrogen atmosphere, into a 1,000 ml four necked flask, LiAlH$_4$ (6.04 g) and THF (300 ml) were added to prepare a suspension of LiAlH$_4$. A THF solution (300 ml) of {2} (40.00 g) was dropwise added thereinto. After completion of the dropwise addition, refluxing and stirring were carried out for 20 hours. After completion of the reaction, water was dropwise added to the reaction solution under cooling with ice, and then, 1N—HCl was added. The oily product was distilled off under reduced pressure, and the obtained solid was recrystallized from acetonitrile to obtain colorless crystals {3} (32.46 g, 86%, mp: 53–54° C.).

$^1$H-NMR(d-DMSO, δppm): 6.44(2H,S), 6.29(1H,S), 5.13 (1H,S), 4.40(2H,d), 3.90(4H,t), 1.67(4H,m), 1.38(4H,m), 1.24(32H,broad), 0.85(6H,t).

Into a 500 ml four necked flask, {3} (30.07 g), triethylamine (6.70 g) and THF (150 ml) were added. Then, a THF solution (100 ml) of 3,5-dinitrobenzoyl chloride (15.29 g) was dropwise added thereto. After completion of the dropwise addition, refluxing and stirring were carried out for 3 hours. The reaction solution was distilled off under reduced pressure and extracted by means of a chloroform, a 1N—NaOH solution and water. The organic layer was distilled off under reduced pressure to obtain slightly yellow crystals {4} (19.45 g, 47%, mp: 61–65° C.).

$^1$H-NMR(d-DMSO, δppm): 9.24(1H,S), 9.18(2H,S), 6.57 (2H,S), 6.46(1H,S), 5.38(2H,S), 3.95(4H,t), 1.77(4H,m), 1.45(4H,m), 1.26(32H,broad), 0.88(6H,t).

Into a 1,000 ml four necked flask, {4} (35.03 g) and 1,4-dioxane (400 ml) were added, and the reactor was flushed with nitrogen, and then PtO$_2$ (0.61 g) was added. Thereafter, the interior of the reactor was adjusted to be a hydrogen atmosphere, and stirring was carried out at 50° C. for 12 hours and at room temperature for 26 hours. After completion of the reaction, PtO$_2$ was removed by filtration, and the filtrate was distilled off under reduced pressure. The residue was recrystallized from n-hexane to obtain slightly yellow crystals {5} (9.89 g, 31%, mp: 55–56° C.).

$^1$H-NMR(d-DMSO, δppm): 6.81(2H,S), 6.41(1H,S), 6.18 (1H,s), 5.21(2H,s), 3.93(4H,t), 1.76(4H,m), 1.42(4H,m), 1.26(32H,broad), 0.88(6H,t).

EXAMPLE 2

Synthesis of Diamine {7}

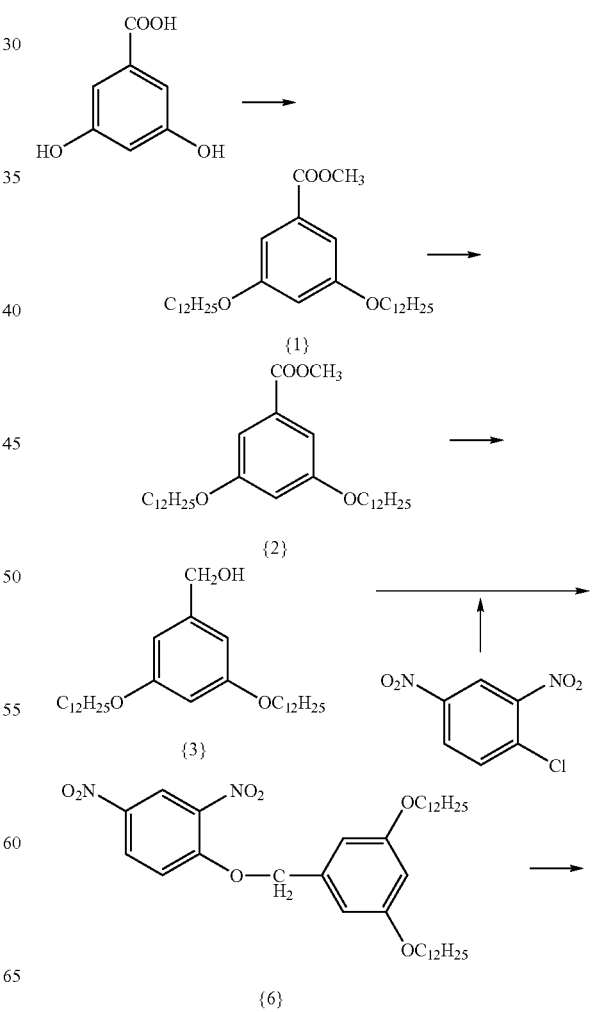

-continued

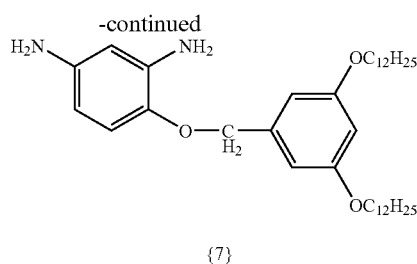

{7}

Into a 500 ml four necked flask, {3} (34.00 g), 2,4-dinitrochlorobenzene (14.51 ml), potassium carbonate (14.80 g), 18-crown ether (7.54 g) and THF (350 ml) were added, and refluxed and stirred for 25 hours. After completion of the reaction, the reaction solution was filtered, and the filtrate was distilled off under reduced pressure. Then, methanol was added to the residue, and precipitated solid was collected by filtration and recrystallized from n-hexane to obtain slightly brown crystals {6} (14.02 g, 31%, 56–58° C.).

$^1$H-NMR(CDCl$_3$, δppm): 8.76(1H,s), 8.37(1H,d), 7.21 (1H,d), 6.55(2H,s), 6.41(1H,s), 5.29(2H,S), 3.93(4H,t), 1.76 (4H,m), 1.44(4H,m), 1.26(32H,broad), 0.88(6H,t).

Into a 500 ml four necked flask, {6} (12.01 g) and 1,4-dioxane (250 ml) were added. The reactor was flushed with nitrogen, and then, PtO$_2$ (0.73 g) was added. Then, the interior of the reactor was changed to a hydrogen atmosphere, followed by stirring at 45° C. for 21 hours and at room temperature for 264 hours. After completion of the reaction, PtO$_2$ was removed by filtration, and the filtrate was distilled off under reduced pressure. The residue was purified by silica gel column chromatography (ethyl acetate/n-hexane=6/4) and recrystallized from n-hexane, to obtain slightly yellow crystals {7} (2.51 g, 20%, mp: 52–53° C.).

$^1$H-NMR(CDCl$_3$, δppm): 6.65(1H,d) , 6.55(2H,s), 6.39 (1H,s), 6.13(1H,s), 6.03(1H,d), 4.89(2H,S), 3.92(4H,t), 3.76 (2H,broad), 3.34(2H,broad), 1.75(4H,m), 1.41(4H,m), 1.24 (32H,broad), 0.88(6H,t).

EXAMPLE 3

Production of Polyimide

PREPARATION EXAMPLE 1

Using the diamine {5} (1.48 g, 2.50 mmol) obtained in Example 1, 2,2'-bis[4-(4-aminophenoxy)phenyl]propane (1.03 g, 2.50 mmol), 1,2,3,4-cyclobutane tetracarboxylic dianhydride (0.98 g, 5.00 mmol) and N-methylpyrrolidone (19.52 g), stirring was carried out at room temperature to carry out a polycondensation reaction to obtain a polyimide precursor solution A having a solid content concentration of 15 wt %. The viscosity of this solution was 1,152 MPa·s (25° C.; by E model viscometer), and the weight average molecular weight as measured by GPC (Gel Permeation Chromatography) was 165,000.

PREPARATION EXAMPLE 2

Using the diamine {5} (0.74 g, 1.25 mmol) obtained in Example 1, 2,2'-bis[4-(4-aminophenoxy)phenyl]propane (1.54 g, 3.75 mmol), 1,2,3,4-cyclobutane tetracarboxylic dianhydride (0.98 g, 5.00 mmol) and N-methylpyrrolidone (18.21 g), stirring was carried out at room temperature to carry out a polycondensation reaction to obtain a polyimide precursor solution B having a solid content concentration of 15 wt %. The viscosity of this solution was 1,293 MPa·s (25° C.; by E model viscometer), and the weight average molecular weight as measured by GPC was 97,600.

PREPARATION EXAMPLE 3

Using the diamine {5} (0.45 g, 0.75 mmol) obtained in Example 1, 2,2'-bis[4-(4-aminophenoxy)phenyl]propane (1.74 g, 4.25 mmol), 1,2,3,4-cyclobutane tetracarboxylic dianhydride (0.98 g, 5.00 mmol) and N-methylpyrrolidone (17.69 g), stirring was carried out at room temperature to carry out a polycondensation reaction to obtain a polyimide precursor solution C having a solid content concentration of 15 wt %. The viscosity of this solution was 5,184 MPa·s (25° C.; by E model viscometer), and the weight average molecular weight as measured by GPC was 413,000.

PREPARATION EXAMPLE 4

Using the diamine {5} (0.15 g, 0.25 mmol) obtained in Example 1, 2,2'-bis[4-(4-aminophenoxy)phenyl]propane (1.95 g, 4.75 mmol), 1,2,3,4-cyclobutane tetracarboxylic dianhydride (0.98 g, 5.00 mmol) and N-methylpyrrolidone (17.17 g), stirring was carried out at room temperature to carry out a polycondensation reaction to obtain a polyimide precursor solution D having a solid content concentration of 16 wt %. The viscosity of this solution was 9,600 MPa·s (25° C.; by E model viscometer), and the weight average molecular weight as measured by GPC was 624,000.

PREPARATION EXAMPLE 5

Using the diamine {7} (1.46 g, 2.50 mmol) obtained in Example 2, 2,2'-bis[4-(4-aminophenoxy)phenyl]propane (1.03 g, 2.50 mmol), 1,2,3,4-cyclobutane tetracarboxylic dianhydride (0.98 g, 5.00 mmol) and N-methylpyrrolidone (19.35 g), stirring was carried out at room temperature to carry out a polycondensation reaction to obtain a polyimide precursor solution E having a solid content concentration of 15 wt %. The viscosity of this solution was 172 MPa·s (25° C.; by E model viscometer), and the weight average molecular weight as measured by GPC was 41,200.

PREPARATION EXAMPLE 6

Using the diamine {7} (0.73 g, 1.25 mmol) obtained in Example 2, 2,2'-bis[4-(4-aminophenoxy)phenyl]propane (1.54 g, 3.75 mmol), 1,2,3,4-cyclobutane tetracarboxylic dianhydride (0.98 g, 5.00 mmol) and N-methylpyrrolidone (18.13 g), stirring was carried out at room temperature to carry out a polycondensation reaction to obtain a polyimide precursor solution F having a solid content concentration of 15 wt %. The viscosity of this solution was 344 MPa·s (25° C.; by E model viscometer), and the weight average molecular weight as measured by GPC was 78,900.

EXAMPLES 4 to 9

Production of Treating Agents for Liquid Crystal Alignment

The polyimide precursor solutions (A to F) obtained in Example 3 (Preparation Examples 1 to 6) were diluted with N-methylpyrrolidone (NMP) or γ-butylolactone (γ-BL) to prepare treating agents for liquid crystal alignment. The results are shown in Table 1.

EXAMPLES 10 to 15

Production of Liquid Crystal Alignment Films

The treating agents for liquid crystal alignment obtained in Examples 4 to 9 were spin-coated on glass substrates and thermally treated at 180° C. or 250° C. to form polyimide coating films. And, the water repellency of the polyimide surface, and the uniformity in alignment and the pretilt angle of liquid crystal when formed into a liquid crystal alignment film, were measured by the following methods. The treating agents for liquid crystal alignment obtained in Examples 4 to 9 were spin-coated on glass substrates having transparent electrodes and thermally treated at 80° C. for 10 minutes and at 180° C. or 250° C. for one hour to form uniform polyimide coating films. The contact angles of water and methylene iodide on such a coating film were measured, and the surface energy was calculated by the following formula.

$$(1+\cos\theta) \times \gamma_L = 2(\gamma_S^d \times \gamma_L^p)^{1/2} + 2(\gamma_S^d \times \gamma_L^p)^{1/2}$$

$$\gamma_L = \gamma_L^d + \gamma_L^p$$

$$\gamma_S = \gamma_S^d + \gamma_S^p$$

θ: The contact angle of the liquid on the coating film
$\gamma_L$: The surface tension of the liquid
$\gamma_L^d$: Dispersion term of the surface tension of the liquid
$\gamma_L^p$: Polarity term of the surface tension of the liquid
$\gamma_S$: The surface tension of the coating film
$\gamma_S^d$: Dispersion term of the surface tension of the coating film
$\gamma_S^p$: Polarity term of the surface tension of the coating film Here, by substituting the contact angle of water as $\theta_1$, the contact angle of methylene iodide as $\theta_2$, the surface tension of water ($\gamma_L=72.8$, $\gamma_L^d=21.8$, $\gamma_L^p=51.0$) (dyn/cm) and the surface tension of methylene iodide ($\gamma_L=50.8$, $\gamma_L^d=49.5$, $\gamma_L^p=1.3$) (dyn/cm), $\gamma_S^d$ and $\gamma_S^p$ were obtained from:

$$(1+\cos\theta_1) \times 72.8 = 2(\gamma_S^d \times 21.8)^{1/2} + 2(\gamma_S^d \times 51.0)^{1/2}$$

$$(1+\cos\theta_2) \times 50.8 = 2(\gamma_S^d \times 49.5)^{1/2} + 2(\gamma_S^d \times 1.3)^{1/2}$$

and the surface energy of the polyimide coating film was calculated from $\gamma_S = \gamma_S^d + \gamma_S^p$.

Further, the measurements of the uniformity in alignment and the pretilt angle of liquid crystal when formed into a liquid crystal alignment film, were carried out by the following methods. The measurement of the pretilt angle was carried out as follows. The polyimide precursor or the polyimide solution was diluted with N-methylpyrrolidone or γ-butyrolactone to obtain a solution having a resin concentration of from 3 to 10 wt %. This solution was spin-coated on a glass substrate having a transparent electrodes and thermally treated at 80° C. for 10 minutes and at 180° C. or 250° C. for one hour to form a uniform polyimide coating film. This coating film was rubbed with a cloth, and then, a pair of such films were assembled with a spacer sandwiched therebetween so that the rubbing directions were in parallel, and liquid crystal (ZLI-2293, manufactured by Merck Company) was injected to prepare a cell having a homeotropic or homogenous alignment. With respect to this cell, after thermal treatment at 95° C. for 5 minutes, the uniformity in alignment of liquid crystal was confirmed by a polarizing microscope, and with respect to one thermally treated at 120° C. for one hour, the pretilt angle was measured by a crystal rotation method or a magnetic field capacity method.

The results are shown in Tables 2 and 3. Further, for the purpose of comparison, the following diamine {8} was synthesized, a polyimide precursor was prepared, further a treating agent for alignment was produced, a liquid crystal alignment film was prepared, and evaluation was carried out. The results are also shown in Tables 1, 2 and 3.

COMPARATIVE EXAMPLE 1

Production of Polyimide

PREPARATION EXAMPLE 7

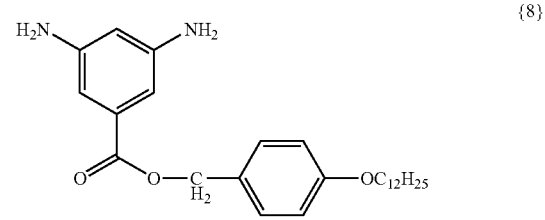

{8}

Using the diamine {8} (1.08 g, 2.50 mmol), 2,2'-bis[4-(4-aminophenoxy)phenyl]propane (1.03 g, 2.50 mmol), 1,2,3,4-cyclobutane tetracarboxylic dianhydride (0.98 g, 5.00 mmol) and N-methylpyrrolidone (17.31 g), stirring was carried out at room temperature to carry out a polycondensation reaction to obtain a polyimide precursor solution G having a solid content concentration of 15 wt %. The viscosity of this solution was 128 MPa·s (25° C.; by E model viscometer), and the weight average molecular weight as measured by GPC was 38,800.

PREPARATION EXAMPLE 8

Using the diamine {8} (0.54 g, 1.25 mmol), 2,2'-bis[4-(4-aminophenoxy)phenyl]propane (1.54 g, 3.75 mmol), 1,2,3,4-cyclobutane tetracarboxylic dianhydride (0.98 g, 5.00 mmol) and N-methylpyrrolidone (17.11 g), stirring was carried out at room temperature to carry out a polycondensation reaction to obtain a polyimide precursor solution H having a solid content concentration-of 15 wt %. The viscosity of this solution was 527 MPa·s (25° C.; by E model viscometer), and the weight average molecular weight as measured by GPC was 76,800.

PREPARATION EXAMPLE 9

Using the diamine {8} (0.33 g, 0.75 mmol), 2,2'-bis[4-(4-aminophenoxy)phenyl]propane (1.74 g, 4.25 mmol), 1,2,3,4-cyclobutane tetracarboxylic dianhydride (0.98 g, 5.00 mmol) and N-methylpyrrolidone (17.03 g), stirring was carried out at room temperature to carry out a polycondensation reaction to obtain a polyimide precursor solution I having a solid content concentration of 15 wt %. The viscosity of this solution was 1,280 MPa·s (25° C.; by E model viscometer), and the weight average molecular weight as measured by GPC was 129,000.

PREPARATION EXAMPLE 10

Using the diamine {8} (0.11 g, 0.25 mmol), 2,2'-bis[4-(4-aminophenoxy)phenyl]propane (1.95 g, 4.75 mmol), 1,2,3,4-cyclobutane tetracarboxylic dianhydride (0.98 g, 5.00 mmol) and N-methylpyrrolidone (16.95 g), stirring was carried out at room temperature to carry out a polycondensation reaction to obtain a polyimide precursor solution J having a solid content concentration of 14 wt %. The viscosity of this solution was 28,160 MPa·s (25° C.; by E model viscometer), and the weight average molecular weight as measured by GPC was 97,600.

COMPARATIVE EXAMPLES 2 TO 5

Production of Treating Agents for Liquid Crystal Alignment

Using the polyimide precursor solutions (G to J) obtained in Comparative Example 1 (Preparation Examples 7 to 10), treating agents for liquid crystal alignment were produced by the same method as in Examples 4 to 9.

COMPARATIVE EXAMPLES 6 to 9

Production of Liquid Crystal Alignment Films

Using the treating agents for liquid crystal alignment obtained in Comparative Examples 2 to 5, liquid crystal alignment films were produced by the same method as in Examples 10 to 15, and the water repellency on the polyimide surface and the uniformity in alignment and the pretilt angle of liquid crystal when formed into a liquid crystal alignment film, were measured.

INDUSTRIAL APPLICABILITY

The diamine compound of the present invention can easily be synthesized, and by using such a compound as a part of the material, it is possible to readily obtain a polyimide precursor and a polyimide having high molecular weights and to modify the surface properties of the polyimide, such as water repellency. Further, a liquid crystal alignment film prepared by using such a treating agent for liquid crystal alignment containing such a polymer, has a high effect to increase the pretilt angle, whereby the desired pretilt angle can readily be obtained.

TABLE 1

Production of treating agents for liquid crystal alignment

| | | Treating agent for liquid crystal alignment | | |
|---|---|---|---|---|
| | Polyimide precursor solution | Solvent for dilution (NMP: γ-BL) | Viscosity (m · Pa · s) | Solid content concentration (wt %) |
| Example | | | | |
| 4 | A | 8:2 | 24.3 | 4.10 |
| 5 | B | 8:2 | 24.9 | 3.98 |
| 6 | C | 8:2 | 28.2 | 2.80 |
| 7 | D | 8:2 | 17.3 | 2.60 |
| 8 | E | 8:2 | 27.7 | 5.67 |
| 9 | F | 8:2 | 35.6 | 4.44 |
| Comparative Example | | | | |
| 2 | G | 8:2 | 21.6 | 7.03 |
| 3 | H | 8:2 | 18.3 | 4.53 |
| 4 | I | 8:2 | 23.9 | 3.90 |
| 5 | J | 8:2 | 22.7 | 2.00 |

TABLE 2

Results of evaluation of the water repellency of coating films

| Treating agent for liquid crystal alignment | | Diamine (amount %) | Contact angle of liquid (°) | | Surface energy (dyn/cm) |
|---|---|---|---|---|---|
| | | | Water | Methylene iodine | |
| Example | Example | | | | |
| 10 | 4 | {5} (50) | 97.7 | 56.1 | 30.8 |
| | | | 93.6 | 52.7 | 32.8 |
| 11 | 5 | {5} (25) | 93.3 | 54.5 | 31.8 |
| | | | 91.8 | 51.5 | 33.5 |
| 12 | 6 | {5} (15) | 87.9 | 51.7 | 33.8 |
| | | | 90.7 | 50.9 | 33.9 |
| 13 | 7 | {5} (5) | 82.5 | 46.6 | 37.2 |
| | | | 82.3 | 41.6 | 39.5 |
| 14 | 8 | {7} (50) | 97.9 | 58.1 | 31.7 |
| | | | 92.5 | 51.8 | 34.7 |
| 15 | 9 | {7} (25) | 95.9 | 54.8 | 33.6 |
| | | | 91.1 | 53.5 | 33.1 |
| Comparative Example | Comparative Example | | | | |
| 6 | 2 | {8} (50) | 89.4 | 51.8 | 33.6 |
| | | | 89.6 | 49.6 | 34.7 |
| 7 | 3 | {8} (25) | 81.9 | 46.2 | 37.5 |
| | | | 82.4 | 42.7 | 39.0 |
| 8 | 4 | {8} (15) | 80.2 | 42.3 | 39.7 |
| | | | 73.8 | 40.5 | 42.1 |
| 9 | 5 | {8} (5) | 72.6 | 30.3 | 46.2 |
| | | | 64.4 | 31.3 | 48.7 |

*The upper represents film formation by thermal treatment at 180° C. for one hour, and the lower represents film formation by thermal treatment at 250° C. for one hour.

TABLE 3

Results of evaluation of the pretilt angle

| Treating agent for liquid crystal alignment | | Diamine (amount %) | Pretilt angle (°) | Pretilt angle (°) After treatment at 120° C. for one hour |
|---|---|---|---|---|
| Example | Example | | | |
| 10 | 4 | {5}(50) | 89.9 | 89.9 |
| | | | 89.7 | 89.1 |
| 11 | 5 | {5}(25) | 89.8 | 89.8 |
| | | | 82.9 | 81.9 |
| 12 | 6 | {5}(15) | 81.6 | 59.2 |
| | | | 62.9 | 42.5 |
| 13 | 7 | {5}(5) | 4.2 | 4.0 |
| | | | 6.3 | 6.9 |
| 14 | 8 | {7}(50) | 89.5 | 89.6 |
| | | | 72.0 | 56.0 |
| 15 | 9 | {7}(25) | 88.3 | 81.6 |
| | | | 69.0 | 65.8 |
| Comparative Example | Comparative Example | | | |
| 6 | 2 | {8}(50) | 89.4 | 89.7 |
| | | | 88.6 | 88.9 |
| 7 | 3 | {8}(25) | 69.4 | 41.4 |
| | | | 34.2 | 12.5 |
| 8 | 4 | {8}(15) | 3.2 | 3.3 |
| | | | 4.8 | 5.9 |

TABLE 3-continued

Results of evaluation of the pretilt angle

| Treating agent for liquid crystal alignment | Diamine (amount %) | Pretilt angle (°) | Pretilt angle (°) After treatment at 120° C. for one hour |
|---|---|---|---|
| 9 | 5 | {8}(5) | 1.3 1.5 |
|  |  |  | 3.6 4.8 |

*The upper represents film formation by thermal treatment at 180° C. for one hour, and the lower represents film formation by thermal treatment at 250° C. for one hour.
*In each cell, uniform alignment without any defect was observed.

The invention claimed is:

1. A polyimide precursor and a polyimide prepared by reacting a tetracarboxylic acid compound or reactive derivative thereof with a diamine reactant, at least portion of which is a diamine compound of formula (1)

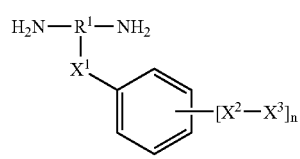

wherein $R^1$ is a trivalent organic group, each of $X^1$ and $X^2$ is a bivalent organic group, $X^3$ is an alkyl or fluoroalkyl group having from 1 to 22 carbon atoms, or a cyclic substituent selected from the group consisting of aromatic rings, aliphatic rings, heterocyclic rings and each of these ring moieties substituted by groups, and n is an integer ranging from 2 to 5.

2. The polyimide precursor and a polyimide according to claim 1, wherein each of $X^1$ is a single bond, —O—, —OCH$_2$—, —CH$_2$O—, —COO—, —OCO—, —COOCH$_2$—, —CH$_2$COO—, —CONH— or —NHCO— and $X^2$ a single bond or —O—.

3. The polyimide precursor and a polyimide according to claim 1, wherein the cyclic substituent of $X^3$ is a benzene ring, a heterocyclic ring, a cyclohexane ring, a biphenyl ring, a terphenyl ring, a bicyclohexyl ring, a tercyclohexyl ring, a phenylcyclohexyl ring, a phenylpyridine ring, a cyclohexylpyridine ring, a phenyldioxane ring, a phenylpyrimidine ring, a cyclohexylpyrimidine ring, a phenylpyrazine ring or a cyclohexylpyrazine ring.

4. A treating agent that enables liquid crystal alignment that contains the polyimide precursor and/or polyimide as defined in claim 1.

5. The treating agent according to claim 4, wherein, when the treating agent is applied to a substrate, the coated substrate is heated to a temperature ranging from 100° to 400° C. to complete imide formation.

6. The treating agent according to claim 4, wherein the treating agent comprises a solvent selected from the group consisting of 2-pyrrolidone, N-methylpyrrolidone, N-ethylpyrrolidone, N,N-dimethylacetoamide, N,N-dimethylformamide, γ-butyrolactone, ethyl cellosolve, butyl cellosolve, ethyl carbitol, butyl carbitol, ethyl carbitol acetate and ethylene glycol.

7. The treating agent according to claim 4, wherein, when the treating agent is applied to a substrate in the formation of a liquid crystal alignment film, the thickness of the resulting film ranges from 0.01 to 1.0 μm.

8. A polyimide precursor and a polyimide prepared by reacting a tetracarboxylic acid compound or reactive derivative thereof with a diamine reactant, at least portion of which is a diamine compound represented by the formula (4):

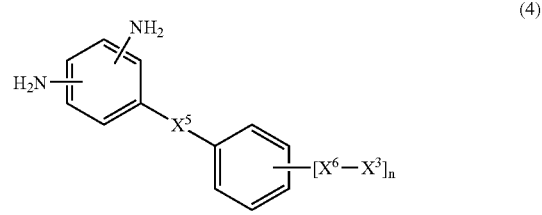

wherein $X^5$ is a bivalent organic group selected from the group consisting of a single bond, —O—, —OCH$_2$—, CH$_2$O—, —COOCH$_2$— and —CH$_2$OOC—, $X^6$ is a bivalent organic group selected from the group consisting of a single bond and —O—, and $X^3$ is an alkyl or fluoroalkyl group having from 1 to 22 carbon atoms, or a cyclic substituent selected from the group consisting of aromatic rings, aliphatic rings, heterocyclic rings and each of these ring moieties substituted by groups, and n is an integer ranging from 2 to 5.

9. A treating agent that enables liquid crystal alignment that contains the polyimide precursor and/or polyimide as defined in claim 8.

10. The treating agent according to claim 9, wherein, when the treating agent is applied to a substrate, the coated substrate is heated to a temperature ranging from 100° to 400° C. to complete imide formation.

11. The treating agent according to claim 9, wherein the treating agent comprises a solvent selected from the group consisting of 2-pyrrolidone, N-methylpyrrolidone, N-ethylpyrrolidone, N,N-dimethylacetoamide, N,N-dimethylformamide, γ-butyrolactone, ethyl cellosolve, butyl cellosolve, ethyl carbitol, butyl carbitol, ethyl carbitol acetate and ethylene glycol.

12. The treating agent according to claim 9, wherein, when the treating agent is applied to a substrate in the formation of a liquid crystal alignment film, the thickness of the resulting film ranges from 0.01 to 1.0 μm.

\* \* \* \* \*